United States Patent
Engelhardt et al.

(10) Patent No.: US 6,806,953 B2
(45) Date of Patent: Oct. 19, 2004

(54) METHOD FOR FLUORESCENCE MICROSCOPY, AND FLUORESCENCE MICROSCOPE

(75) Inventors: Johann Engelhardt, Bad Schoenborn (DE); Juergen Hoffmann, Bad Camberg (DE)

(73) Assignee: Leica Microsystems Heidelberg GmbH, Mannheim (DE)

(*) Notice: Subject to any disclaimer, the term of this patent is extended or adjusted under 35 U.S.C. 154(b) by 0 days.

(21) Appl. No.: 10/268,159

(22) Filed: Oct. 9, 2002

(65) Prior Publication Data

US 2003/0071226 A1 Apr. 17, 2003

(30) Foreign Application Priority Data

Oct. 12, 2001 (DE) .......................................... 101 50 542

(51) Int. Cl.[7] .............................................. G01N 21/64
(52) U.S. Cl. ..................................... 356/317; 250/459.1
(58) Field of Search ................................ 356/317–318, 356/417; 250/458.1–461.2

(56) References Cited

U.S. PATENT DOCUMENTS

| | | | | |
|---|---|---|---|---|
| 5,591,981 A | * | 1/1997 | Heffelfinger et al. | .... 250/458.1 |
| 6,097,870 A | | 8/2000 | Ranka et al. | ................ 385/127 |
| 6,134,002 A | * | 10/2000 | Stimson et al. | ............. 356/318 |
| 6,300,639 B1 | | 10/2001 | Wiederhoeft | ............. 250/458.1 |
| 2001/0025930 A1 | | 10/2001 | Engelhardt et al. | ...... 250/459.1 |
| 2001/0028455 A1 | * | 10/2001 | Uhl | ............................. 356/317 |
| 2002/0155592 A1 | * | 10/2002 | Kelleher et al. | ......... 435/288.7 |

FOREIGN PATENT DOCUMENTS

| | | |
|---|---|---|
| DE | 19853669 | 5/1999 |
| DE | 19902625 | 9/1999 |
| DE | 19906757 | 12/1999 |
| DE | 19829944 | 1/2000 |
| DE | 19853407 | 5/2000 |
| DE | 10015121 | 10/2001 |
| EP | 0495930 | 5/1999 |

* cited by examiner

Primary Examiner—F. L. Evans
Assistant Examiner—Kara Geisel
(74) Attorney, Agent, or Firm—Davidson, Davidson & Kappel, LLC

(57) ABSTRACT

The invention discloses a fluorescence microscope comprising a light source that emits excitation light for illumination of a specimen, means for defining a two-dimensional search region for the excitation and detection wavelengths, means for selecting a subregion from the search region, at least one detector that detects detected light proceeding from the specimen, and a display for displaying an image of at least a portion of the specimen. Furthermore the invention discloses a method for fluorescence microscopy.

23 Claims, 3 Drawing Sheets

METHOD FOR FLUORESCENCE MICROSCOPY, AND FLUORESCENCE MICROSCOPE

CROSS REFERENCE TO RELATED APPLICATIONS

This application claims priority of the German patent application 101 50 542.6 which is incorporated by reference herein.

FIELD OF THE INVENTION

The invention concerns a method for fluorescence microscopy, wherein a specimen is illuminated with excitation light, wherein detected light proceeding from the specimen is detected, and wherein an image of at least a portion of the specimen is generated The invention furthermore concerns a fluorescence microscope.

BACKGROUND OF THE INVENTION

In incident-light fluorescence microscopy, that component of the light of a light source, e.g. an arc lamp, which exhibits the desired wavelength range for fluorescence excitation is coupled into the microscope beam path using a color filter (called the excitation filter). Incoupling into the microscope's beam path is accomplished using a dichroic beam splitter which reflects the excitation light to the specimen while it allows the fluorescent light proceeding from the specimen to pass largely unimpeded. The excitation light backscattered from the specimen is held back with a blocking filter that is, however, transparent to the fluorescent radiation. Optimum combination of mutually coordinated filters and beam splitters into an easily exchangeable modular filter block has been common for some time. The filter blocks are usually arranged in a revolving turret within the microscope as part of so-called incident-light fluorescence illuminators, thus making possible quick and simple exchange.

The German Patent Application 199 06 757 A1 discloses an optical arrangement in the beam path of a light source suitable for fluorescence excitation, preferably in the beam path of a confocal laser scanning microscope, having at least one spectrally selective element for coupling the excitation light of at least one light source into the microscope and for blocking the excitation light or excitation wavelength scattered and reflected at the specimen out of the light coming from the specimen via the detection beam path. For variable configuration with a very simple design, the optical arrangement is characterized in that excitation light of different wavelengths can be blocked out by way of the spectrally selective element. Alternatively, an optical arrangement of this kind is characterized in that the spectrally selective element can be set to the excitation wavelength that is to be blocked out. The selective element is preferably configured as an acoustooptical element. Arrangements of this kind are often referred to as acoustooptical beam splitters (AOBS).

In scanning microscopy, a specimen is scanned with a light beam. Lasers are often used as the light source for this purpose. EP 0 495 930: "Confocal microscope system for multicolor fluorescence," for example, discloses an arrangement having a single laser that emits several laser lines. Mixed-gas lasers, in particular ArKr lasers, are used most often at present for this purpose.

Solid-state lasers and dye lasers, as well as fiber lasers and optically parametric oscillators (OPO) preceded by a pumping laser, are also often used.

The German Patent Application DE 198 53 669 A1 discloses an ultrashort pulse source with controllable multiple wavelength output that is utilized in particular in a multi-photon microscope. The system comprises an ultrashort-pulse laser for generating ultrashort optical pulses of a fixed wavelength, and at least one wavelength conversion channel.

U.S. Pat. No. 6,097,870 discloses an arrangement for generating a broadband spectrum in the visible spectral region. The arrangement is based on a microstructured fiber into which the light of a pump laser is coupled. The wavelength of the pump light is modified in the microstructured fiber in such a way that the resulting spectrum comprises wavelengths both above and below the wavelength of the pump light.

So-called photonic band gap material or photon crystal fibers, "holey" fibers, or microstructured fibers are also used as the microstructured material. Embodiments as "hollow fibers" are also known.

The specimens examined are, for example, biological tissues or sections prepared with fluorescent dyes. Photomultipliers or semiconductor detectors are usually used as the detectors. For simultaneous detection of detected light of several detection wavelengths, the detected light is spatially distributed to several detectors using color beam splitters.

The German Patent Application 199 02 625 A1 discloses an apparatus for simultaneous detection of multiple spectral regions of a light beam, in particular for detection of the light beam of a laser scanner in the detection beam path of a confocal microscope. In order to achieve a simple configuration with small overall size while eliminating the defocusing effect, the apparatus is characterized by an arrangement for spectral spreading of the light beam and by an arrangement for splitting the spread beam out of the dispersion plane into spectral regions, and for subsequent detection of the split-out spectral regions. Apparatuses of this kind belong to the species of multiband detectors.

One particular difficulty in fluorescence microscopy is that of discovering, for a specimen prepared with fluorescent dyes, the appropriate excitation wavelength and appropriate detection wavelength under given boundary conditions. At present, the excitation wavelengths are determined empirically from among the (usually few) available excitation wavelengths. For that reason, and as a result of the nature of the light sources, the selected excitation light is limited to a few individual lines. In exactly the same way, suitable detection wavelengths in which the detectors detect are determined by iterative experimentation in combination with different excitation wavelengths. An optimum combination of excitation and detected light is not found in this fashion. The results are unnecessarily rapid bleaching of the specimen and poor imaging quality.

SUMMARY OF THE INVENTION

It is therefore the object of the invention to describe a method that makes possible efficient, low-specimen-impact fluorescent imaging of a specimen with optimized image quality.

The object is achieved by way of a method for fluorescence microscopy, wherein a specimen is illuminated with excitation light, wherein detected light proceeding from the specimen is detected, and wherein an image of at least a portion of the specimen is generated, comprising the steps of:

defining a two-dimensional search region for excitation and detection wavelengths;

determining, from the image of the specimen, quality features for subregions of the search region;

selecting a subregion on the basis of the quality features that have been determined;

illuminating the specimen with excitation light of the excitation wavelengths of the selected subregion; and detecting the detected light of the detection wavelengths of the selected subregion.

It is also an object of the invention to describe a fluorescence microscope that makes possible efficient, low-specimen-impact fluorescent imaging of a specimen with optimized image quality.

The object is achieved by way of a fluorescence microscope comprising:

a light source that emits excitation light for illumination of a specimen, means for defining a two-dimensional search region for the excitation and detection wavelengths, means for selecting a subregion from the search region, at least one detector that detects detected light proceeding from the specimen, and a display for displaying an image of at least a portion of the specimen.

The invention has the advantage of making possible optimized fluorescent excitation and detection, eliminating unnecessarily rapid bleaching of the specimen's fluorescent dyes. Another advantage also achieved thereby is that not only suitable discrete excitation lines and suitable discrete detected light lines, but also suitable optimum ranges of excitation wavelengths and detection wavelengths are determined in dye-specific fashion.

In a preferred embodiment, the method contains the further step of storing the parameters characterizing the subregion so they can be taken into account in later examinations and image processing steps.

In a variant embodiment, the method comprises the additional previous steps of acquiring an overview image and selecting an image region from the overview image. This has the advantage that the excitation wavelength or detection wavelength can be determined for specific regions of the specimen that are of particular interest to the user or have been especially prepared.

In a preferred embodiment, the search region is varied during the determination of quality features. The quality features can be, in particular, the brightness, contrast, resolution, sharpness, or lifetime of the image, or combinations of these variables.

Means for determining quality features from the image of the specimen are provided in the fluorescence microscope. In the context of a scanning microscope, the scanning speed, scan rate, pixel size of the image in terms of specimen segment size, over- and undersampling, and pinhole size (in the case of a confocal microscope), among other factors, are to be taken into consideration here.

For determination of the variables to be displayed, the intensity data of the detected light of at least two successively acquired data are analyzed. One method for determining the bleaching rate is based on plotting the frequencies H of occurrence of various intensities I, for both the first ($I_1$) and second ($I_2$), on respective intensity histograms, and calculating the respective histogram center points, which are identical to the average pixel intensity of the respective image.

Shifting the histogram center point allows the bleaching factor $B=1-I_1/I_2$ to be calculated and displayed to the user. Bar charts that can be shown on a display are advantageous for this purpose.

It is possible to determine the degree of saturation of the fluorescent dyes only by modifying the system parameters, for example the illuminating light power level. If the fluorescent dyes are not yet completely at saturation, an increase in the illuminating light power level, preferably by a few percent, results in a steeper ($I_1$, $I_2$) line. If the selected illuminating light power level lies within the linear region of the quantum yield distribution, the ratio of the slopes of the correlation lines is equal to the ratio of the illuminating light power level for the scan of image 1 to that for the scan of image 2. A deviation from this equality can be used (and displayed) as an indicator of the degree of saturation.

The display apparatus that is preferably provided for displaying the quality features contains graphical elements, such as graphs or bar charts, depicted on a display. Display can also be performed numerically. The search region is also preferably depicted graphically on a display, for example as an area in a Cartesian coordinate system; changes in the search region are made by the user by modifying the area with a pointing device, for example a PC mouse.

The subregions are preferably determined automatically. An apparatus for automatically determining suitable subregions, which takes into account in particular the bleaching behavior and degree of saturation, is provided for the purpose.

The apparatus for automatic selection of the subregion contains a computer that pursues a definable search strategy on the basis of a definable algorithm. The selected subregion defines the excitation wavelengths of the excitation light. This is preferably a wavelength band.

In a preferred embodiment, a light source that contains a microstructured optical element, for example made of photonic band gap material, is used to generate broadband excitation light. In a preferred embodiment of the scanning microscope, the microstructured optical element is constructed from a plurality of microoptical structural elements that exhibit at least two different optical densities. An embodiment in which the optical element contains a first region and a second region, the first region having a homogeneous structure and a microscopic structure made up of microoptical structural elements being formed in the second region, is very particularly preferred. It is also advantageous if the first region surrounds the second region. The microoptical structural elements are preferably cannulas, lands, honeycombs, tubes, or cavities. In another embodiment, the microstructured optical element is made of glass or plastic material and cavities arranged next to one another. Particularly preferred is the variant embodiment in which the microstructured optical element is made of photonic band gap material and is configured as a light-guiding fiber. An optical diode, which suppresses return reflections of the light beam that arise from the ends of the optical light-guiding fiber, is preferably provided between the laser and the light-guiding fiber. A variant embodiment that is very particularly preferred and easy to implement contains as the microstructured optical element a conventional light-guiding fiber, having a fiber core diameter of approx. 9 $\mu$m, which exhibits a taper along at least a portion. Light-guiding fibers of this type are known as "tapered fibers." Preferably the light-guiding fiber is a total of 1 m long, and exhibits a taper over a length of from 30 mm to 90 mm. In a preferred embodiment, the diameter of the light-guiding fiber in the region of the taper is approx. 2 $\mu$m. The fiber core diameter is correspondingly in the nanometer range. In a very preferred embodiment, in particular with a light source that contains microstructured optical material, a pulsed laser is provided that preferably emits light pulses of a pulse energy that exceeds 1 nJ.

In another variant embodiment, the light source contains a mixed-gas laser that is capable of emitting laser light of different wavelengths. The laser can also be embodied as a solid-state, gas, or dye laser, or as an optically parametric oscillator (OPO).

In a preferred embodiment of the fluorescence microscope, the light source contains a selection means for selecting the excitation wavelengths. The selection means is preferably an acoustooptical element, for example an acoustooptical tunable filter (AOTF), an acoustooptical deflector (AOD), or an acoustooptical tunable filter (AOBS). The selection means can also comprise an interference filter, a prism, a liquid-crystal filter, a polarization filter, a Fabry-Perot filter, a Sagnac filter, or a color beam splitter.

The light source preferably contains an apparatus for varying the power level of the excitation light. It is very particularly advantageous in this context to configure the light source in such a way that the power level of the excitation light can be varied or completely blocked out in terms of at least one selectable wavelength or at least one selectable wavelength range. An embodiment in which the excitation light of the selected subregion is generated by spatially spectral splitting of primary light of the light source, and with a suitable variable stop arrangement or filter arrangement that suppresses or entirely blocks out spectral components, the remaining spectral components then being combined again into an excitation light beam, is very particularly advantageous. A prism or a grating, for example, can be used for spatially spectral splitting.

An embodiment that comprises an operating element for setting the light power level and the spectral composition of the excitation light of the selected subregion is particularly advantageous. This can be a control panel or a PC. The setting data are transferred to the apparatus for illumination or to the apparatus for varying the power level of the spectrally spread light preferably in the form of electrical signals. Setting by way of sliders, which are displayed on a display of a PC and operated e.g. with a computer mouse, is particularly intuitive.

In a preferred embodiment, a memory is provided in which data regarding the subregion and the quality features can be stored.

The detected light contains the detection wavelengths of the subregion. Preferably the detected light comprises at least one wavelength band. In a preferred embodiment, the detector is embodied as a multiband detector that, preferably by spatially spectral splitting of the detected light, makes possible multichannel detection. The detector contains at least one photomultiplier or one semiconductor detector.

In a particular variant embodiment, the detector contains a selection means for selecting the detection wavelengths, which can be embodied as an acoustooptical element or an interference filter or a prism or liquid-crystal filter or polarization filter or Fabry-Perot filter or Sagnac filter or color beam splitter.

In a very particularly preferred embodiment, the fluorescence microscope is a confocal microscope.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
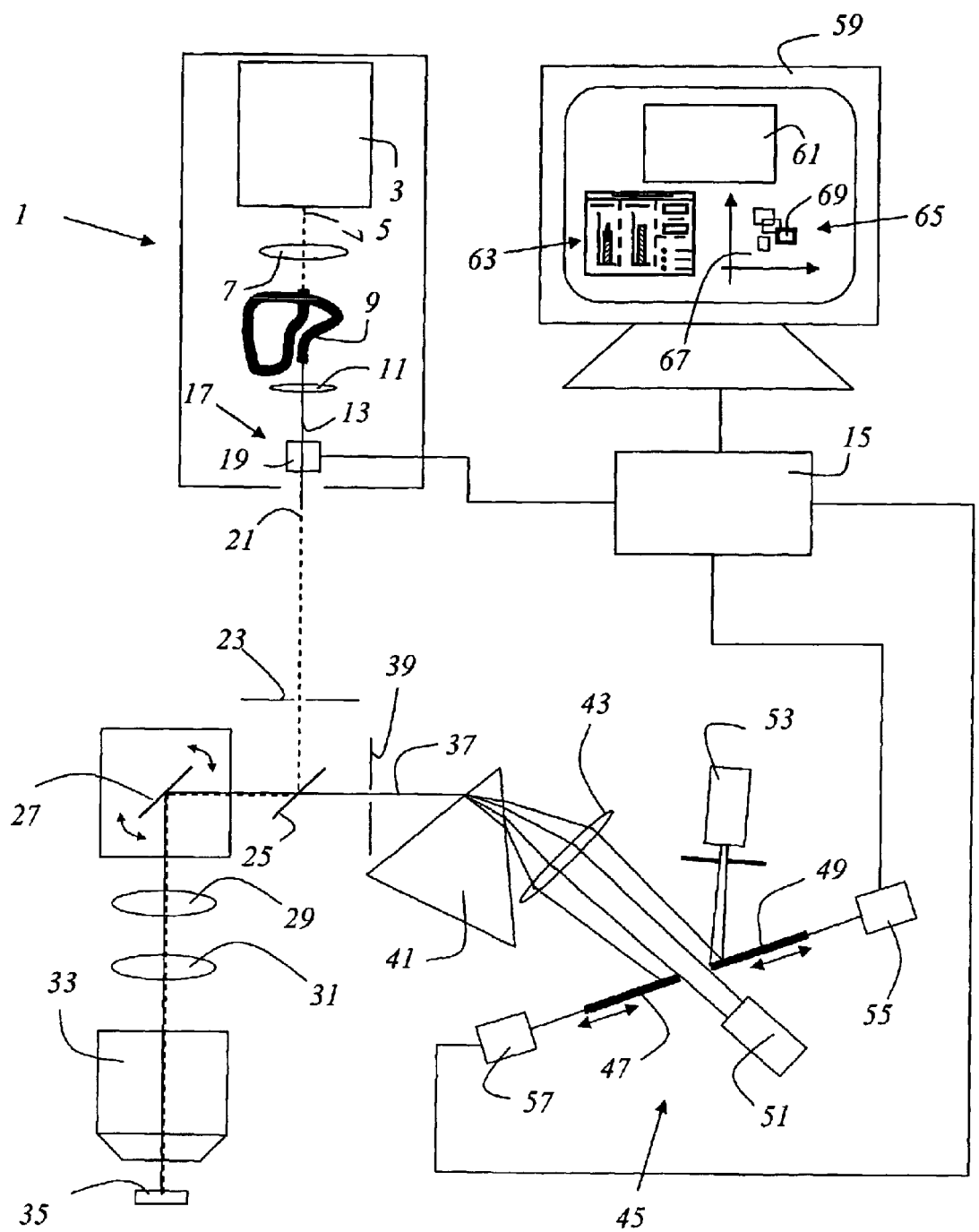
FIG. 1 shows a confocal scanning microscope according to the present invention.

FIG. 1 shows a fluorescence microscope according to the present invention that is embodied as a confocal scanning microscope. The fluorescence microscope comprises a light source 1 which contains a laser 3 that is embodied as a diode-laser-pumped, mode-coupled titanium-sapphire laser and emits a pulsed light beam 5 which is drawn as a dashed line. The duration of the light pulses is approx. 100 fs at a repetition rate of 80 MHz. Light beam 5 is focused with focusing optical system 7 onto a microstructured optical element 9 that comprises a light-guiding fiber made of photonic band gap material. In the microstructured optical element, the light of the laser is spectrally spread. The spectrally spread light emerging from light-guiding fiber 9 is shaped with the aid of optical system 11 into a collimated, spectrally spread light beam 13. The spectrum of the spectrally spread light extends from approx. 300 nm to 1600 nm, the light power level being largely constant over the entire spectrum. A computer 15 controls a selection means 17, which is embodied as an acoustooptical tunable filter (AOTF) 19, in accordance with the selected subregion. Excitation light beam 21 emerging from light source 1 comprises the excitation wavelengths of the selected subregion.

Excitation light beam 21 is focused onto an illumination pinhole 23 and travels via main beam splitter 25 to scanning mirror 27, which guides excitation light beam through scanning optical system 29, tube optical system 31, and objective 33 over specimen 35. Detected light 37 proceeding from specimen 35, which is depicted with dashed lines in the Figure, travels through objective 33, tube optical system 31, and scanning optical system 29 back to scanning mirror 27 and then to main beam splitter 25, passes through the latter, and after passing through detection pinhole 39 with prism 41 is spatially spectrally split and then focused by field lens 43. Prism 41 is a constituent of multiband detector 45, which, with mirror stops 47, 49, conveys various spectral components of the detected light to photomultipliers 51 and 53. The spectral components correspond to the detection wavelengths of the selected subregion. Mirror stops 47, 49 are moved with positioning motors 55, 57, which are controlled by computer 15 in accordance with the selected subregion. Multiband detector 45 preferably contains substantially more channels, but for better clarity only two channels are shown. The quality parameters of image 61 are displayed on monitor 59 in a first dialog window 63. Search region 67 in the form of a coordinate system, and the selected subregion 69, are displayed in a second dialog window 65.

Figure 2:
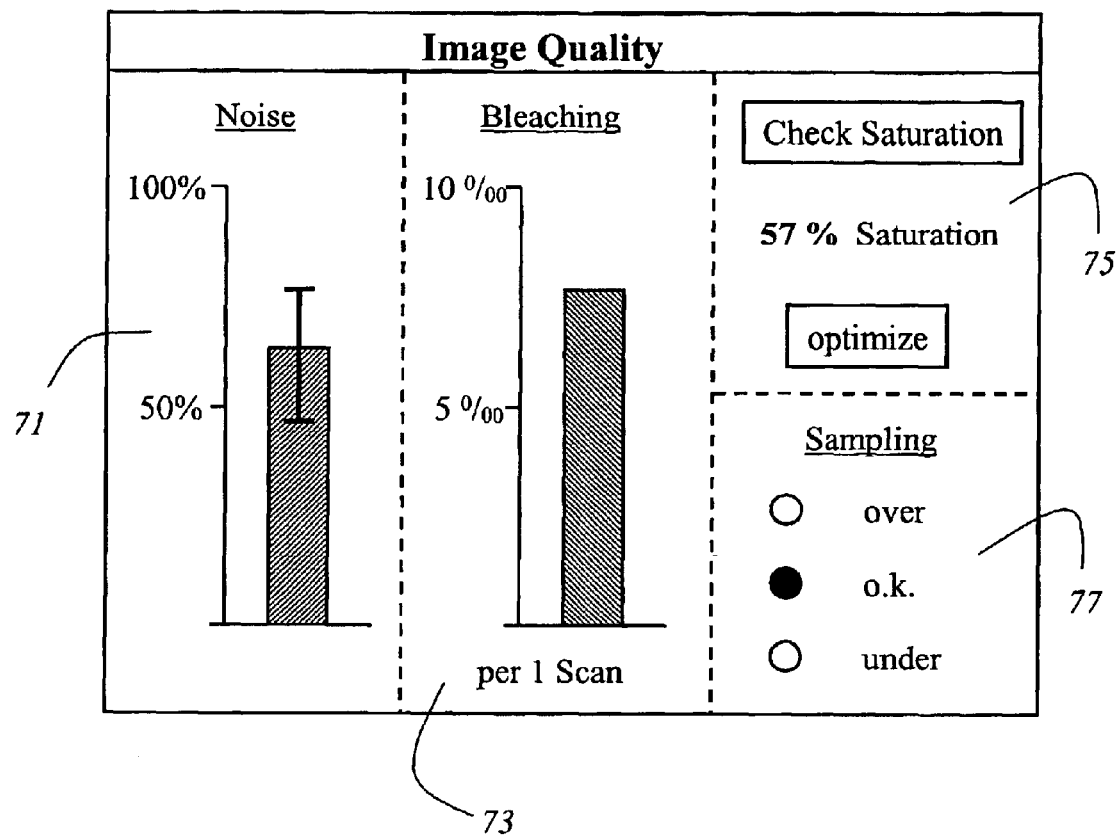
FIG. 2 shows an embodiment of the screen display of the quality parameters.

FIG. 2 shows an embodiment of the screen display of quality parameters, which is displayed on monitor 59 in a first dialog window 65. The noise characteristics of the specimen are displayed in a first subwindow 71 in the form of a bar graph. The bleaching rate of the fluorochrome is displayed in a second subwindow 73 in the form of a further bar graph. The saturation of the fluorochrome (as a percentage) is indicated in third subwindow 75. A fourth subwindow 77 indicates whether over- or undersampling exists.

Figure 3:
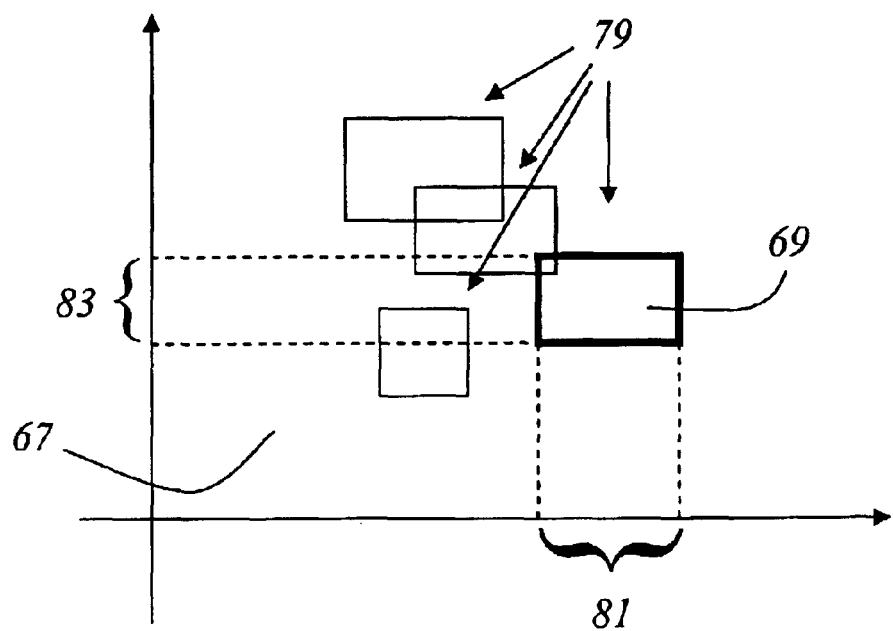
FIG. 3 depicts the search region and various subregions.

FIG. 3. depicts the search region and various subregions 79 in the form of a coordinate system 65 in which excitation wavelengths 81 of the selected subregion 69 are shown on the abscissa, and detection wavelengths 83 of the selected subregion 69 on the ordinate. Selection of the subregion is preferably performed automatically on the basis of the quality parameters that have been determined. For better clarity, subregions 79 are depicted in the form of rectangles. In general, these are substantially more complex, noncontinuous shapes.

The invention has been described with reference to a particular exemplary embodiment. It is self-evident, however, that changes and modifications can be made without thereby leaving the range of protection of the claims below.

What is claimed is:

1. A method for fluorescence microscopy, wherein a specimen is illuminated with excitation light, wherein detected light proceeding from the specimen is detected, and wherein an image of at least a portion of the specimen is generated, comprising the steps of:

defining a two-dimensional search region for excitation and detection wavelengths;

determining, from the image of the specimen, quality features for subregions of the search region, the quality features being at least one of a brightness, a contrast, a resolution, a sharpness and a lifetime of the image;

selecting a subregion on the basis of the quality features that have been determined;

illuminating the specimen with excitation light of the excitation wavelengths of the selected subregion; and detecting the detected light of the detection wavelengths of the selected subregion.

2. The method as defined in claim 1, further comprising the step of:

storing parameters characterizing the subregion.

3. The method as defined in claim 1, further comprising the steps of:

acquiring an overview image; and selecting an image region from the overview image.

4. The method as defined in claim 1, wherein the search region is varied during the determination of quality features.

5. A fluorescence microscope comprising:

a light source that emits excitation light for illumination of a specimen, means for defining a two-dimensional search region for the excitation and detection wavelengths, means for selecting a subregion from the search region based on quality features determined from the image of the specimen, the quality features being at least one of a brightness, a contrast, a resolution, a sharpness and a lifetime of the image, at least one detector that detects detected light proceeding from the specimen, and a display for displaying an image of at least a portion of the specimen.

6. The fluorescence microscope as defined in claim 5, further comprising means for determining the quality features from the image of the specimen.

7. The fluorescence microscope as defined in claim 5, further comprising a display apparatus for displaying the quality features.

8. The fluorescence microscope as defined in claim 5, wherein the means for selecting a subregion includes an apparatus for automatically selecting suitable subregions.

9. The fluorescence microscope as defined in claim 8, wherein the apparatus for automatic selection of the subregion contains a computer that pursues a definable search strategy on the basis of a definable algorithm.

10. The fluorescence microscope as defined in claim 5, wherein the excitation light comprises the excitation wavelengths of the selected subregion.

11. The fluorescence microscope as defined in claim 10, wherein the excitation light comprises a wavelength band.

12. The fluorescence microscope as defined in claim 5, wherein the light source contains photonic band gap material.

13. The fluorescence microscope as defined in claim 5, wherein the light source contains a microstructured light-guiding fiber.

14. The fluorescence microscope as defined in claim 5, wherein the light source contains a selection means for selecting the excitation wavelengths.

15. The fluorescence microscope as defined in claim 14, wherein the selection means consists essentially of an acoustooptical element or an interference filter or a prism or a liquid-crystal filter or a polarization filter or a Fabry-Perot filter or a Sagnac filter or a color beam splitter.

16. The fluorescence microscope as defined in claim 5, further comprising a memory, in which data regarding the subregion and the quality features can be stored.

17. The fluorescence microscope as defined in claim 5, wherein the detected light comprises detection wavelengths of the subregion.

18. The fluorescence microscope as defined in claim 17, wherein the detected light comprises at least one wavelength band.

19. The fluorescence microscope as defined in claim 5, wherein the detector is a multiband detector.

20. The fluorescence microscope as defined in claim 5, wherein the detector contains a means for spatial splitting of the detected light.

21. The fluorescence microscope as defined in claim 5, wherein the detector contains a selection means for selecting the detection wavelengths.

22. The fluorescence microscope as defined in claim 21, wherein the selection means consists essentially of an acoustooptical element or an interference filter or a prism or a liquid-crystal filter or a polarization filter or a Fabry-Perot filter or a Sagnac filter or a color beam splitter.

23. The fluorescence microscope as defined in claim 5, wherein the fluorescence microscope is a confocal scanning microscope.

* * * * *